(12) United States Patent
Becker et al.

(10) Patent No.: US 6,380,133 B2
(45) Date of Patent: *Apr. 30, 2002

(54) MICROENCAPSULATED CLOMAZONE IN THE PRESENCE OF FAT AND RESIN

(75) Inventors: John M. Becker, Flemington; Janos Szamosi, Washington; Hylsa E. Garcia, Elizabeth, all of NJ (US)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/778,280

(22) Filed: Feb. 6, 2001

Related U.S. Application Data

(62) Division of application No. 09/521,514, filed on Mar. 8, 2000, now Pat. No. 6,218,339.
(60) Provisional application No. 60/125,044, filed on Mar. 18, 1999.

(51) Int. Cl.$^7$ .......................... A01N 43/02; A01N 43/80
(52) U.S. Cl. ....................................... 504/140; 504/265
(58) Field of Search .................................. 504/140, 265

(56) References Cited

U.S. PATENT DOCUMENTS 5,310,721 A * 5/1994 Lo .............................. 504/116

* cited by examiner

*Primary Examiner*—Alton Pryor
(74) *Attorney, Agent, or Firm*—FMC Corporation

(57) ABSTRACT

The present invention provides herbicidal formulation that is composed of an aqueous liquid having suspended therein a multitude of microcapsules having a capsule wall of a porous polymer encapsulating a solution of clomazone, and suitable concentrations of fat in the absence of a resin, or a resin in the absence of a fat, or both fat and resin. Preferably, if included, the fat is at least 95% saturated.

13 Claims, No Drawings

MICROENCAPSULATED CLOMAZONE IN THE PRESENCE OF FAT AND RESIN

This application is a Divisional Application of, prior application Ser. No. 09/521,514 filed on Mar. 8, 2000, now U.S. Pat. No. 6,218,339, which claims the benefit of U.S. Provisional Application Ser. No. 60/125,044 filed Mar. 18, 1999.

The present invention relates generally to the field of herbicidal chemical compositions. In particular, the present invention relates to novel compositions of a known herbicidal compound, namely clomazone, designed to reduce clomazone's characteristic volatility, thereby reducing risk of unintended herbicidal activity when clomazone is applied.

Clomazone (2-[(2-chlorophenyl)methyl]-4,4-dimethyl-3-isoxazolidinone) is a well-known herbicide commercially available for controlling many broadleaf and most grass weeds, and has been found to have selective characteristics making it particularly useful for the control of weeds when growing soybean, cotton, sugarcane, rice, tobacco, oilseed rape, vegetables and others. Clomazone can be phytotoxic to some non-targeted crops and naturally occurring plant species when applied to control undesired vegetation. Contact of clomazone with such unintended crops is the result of vapor transfer of the clomazone to sensitive species growing in adjacent areas.

Although clomazone can be, and is, sold with suitable label instructions to prevent exposure to sensitive crops, measures that will further decrease the exposure of the non-targeted crops to clomazone without substantial diminution of herbicidal efficacy against weeds will greatly expand the usefulness of clomazone and thus result in lower overall costs.

Other microencapsulated formulations of clomazone exist that are intended to control the volatile nature of the herbicide. See, e.g., U.S. Pat. Nos. 5,597,780, 5,583,090, and 5,783,520. Unfortunately, these formulations do not provide optimum herbicidal efficacy when compared to commercially available clomazone 4 pound/gallon emulsifiable concentrate (4.0EC) formulation. Given the commercial value of clomazone, improved formulations are therefore needed.

SUMMARY OF THE INVENTION

The present invention is directed to herbicidal formulations comprising microcapsules suspended in an aqueous liquid medium, wherein the microcapsules comprise a porous polymer wall, clomazone, and a fat, or resin. Different embodiments of the present invention include suitable concentrations of fat in the absence of resin, or resin in the absence of fat, or both fat and resin. Preferably, if included, the fat is at least 95% saturated. The present invention is also directed to said formulations wherein the porous polymer wall is, in part, the reaction product of the resin and a polyisocyanate. These formulations provide for the application of clomazone to undesirable vegetation encountered in the cultivation of various plant species, particularly agronomic crops, while minimizing off-target vapor transfer of the herbicide. Accordingly, embodiments of the present invention provide sufficient herbicidal efficacy with respect to unwanted vegetation, yet avoid the aforementioned problems seen in currently available formulations of clomazone.

In a first embodiment of the present invention there is provided an aqueous dispersion of microcapsules containing a herbicidally effective amount of clomazone in the presence of a highly saturated fat that is at least about 95% saturated.

In a second embodiment of the present invention there is provided formulations containing a herbicidally effective amount of clomazone wherein the microcapsule formed is, in part, the reaction product of a styrene-maleic anhydride copolymer resin and a polyfunctional polyisocyanate.

In a third embodiment of the present invention there is provided formulations containing a herbicidally effective amount of clomazone in the presence of a highly saturated fat that is at least about 95% saturated, and wherein the microcapsule formed is, in part, the reaction product of a styrene-maleic anhydride copolymer resin and a polyfunctional polyisocyanate.

Preferably, in those formulations containing it, the fat is at least about 98% saturated. Examples of such fats include, without limitation, waxes, suet, lard or tallow. The encapsulant is a porous condensate polymer of polyurea, polyamide or amide-urea copolymer. To provide acceptable volatility control without unacceptable sacrifice of herbicidal efficacy, the percentage of polymer comprising the microcapsules ranges from about 5 percent to about 35 percent by weight, preferably about 10 percent to about 25 percent by weight. Also the percentage of highly saturated fat of the encapsulated material ranges from about 0.5 percent to about 12 percent by weight of the organic phase, preferably about 1 percent to about 8 percent by weight, more preferably about 2 percent to about 6 percent by weight.

The microcapsules of the present invention provide volatility reduction of about 20–90 percent as compared with clomazone prepared and applied from an emulsifiable concentrate, which is commercially available. The microcapsules of the present invention also provide increased herbicidal efficacy against certain weed species from about one to about four times that of known clomazone microcapsule formulations that are also commercially available. Thus, the practice of the present invention, among other things, enables one to apply clomazone to the appropriate locus for control of weeds in crops while eliminating or substantially diminishing the risk of clomazone injury to plant species located in areas adjacent thereto without the need to resort to expensive and time-consuming pre-plant incorporation or special application procedures.

DEFINITIONS

The modifier "about" is used herein to indicate that certain preferred operating ranges, such as ranges for molar ratios for reactants, material amounts, and temperature, are not fixedly determined. The meaning will often be apparent to one of ordinary skill. For example, a recitation of a temperature range of about 120° C. to about 135° C. in reference to, for example, a range of temperature for a chemical reaction would be interpreted to include other like temperatures that can be expected to favor a useful reaction rate for the reaction, such as 105° C. or 150° C. Where guidance from the experience of those of ordinary skill is lacking, guidance from the context is lacking, and where a more specific rule is not recited below, the "about" range shall be not more than 10% of the absolute value of an end point or 10% of the range recited, whichever is less.

The term "ambient temperature" refers to a temperature in the range of about 20° C. to about 30° C. As used herein, the terms "crop", or "crops", "plant" or "plants" are one and the same, and refer to plants of interest or plant products derived thereof that are grown for ornamental, industrial or food uses. The terms "weed" or "vegetation" are one and the same, and refer to an unwanted plant or plants that are growing in a place or in a manner that is detrimental to a plant or plants of interest. The term "suet" refers to a hard fat found, for example, around the kidneys and loins of beef and mutton, or cattle, from which tallow is derived. The term "tallow" refers to a rendered fat from said cattle. The term "lard" refers to a soft, solid or semi-solid fat obtained by rendering fatty tissue of hogs. The term "CS" or "CS formulation" refers to a microcapsule or capsule suspension formulation of clomazone. The term, for example, "3.0 CS" or "3.0 CS formulation" refers to a microcapsule or capsule suspension formulation of clomazone containing 3.0 pounds of clomazone/gallon of finished formulation. The term "resin" refers to a chemical polymer with a molecular weight of about 100,000 to about 400,000. The term "cross-linking" refers to the chemical bonding between two adjacent polymer chains.

DETAILED DESCRIPTION OF THE INVENTION

The formulations of clomazone, in a first embodiment of the present invention, provide an aqueous suspension of microcapsules containing clomazone in combination with a highly saturated fat that is at least about 95% saturated.

In a second embodiment of the present invention there is provided formulations of clomazone wherein the microcapsule formed is, in part, the reaction product of a suitable resin and a polyfunctional polyisocyanate, wherein the resin is suitable if it acts both as an emulsifier and a cross-linker with the polyisocyanate. Preferred such resins include the copolymerization products of styrene and maleic anhydride.

In a third embodiment of the present invention there is provided formulations of clomazone in the presence of a highly saturated fat that is at least about 95% saturated, and wherein the microcapsule formed is, in part, the reaction product of a suitable resin and a polyfunctional polyisocyanate, which functions as described, supra.

A highly saturated fat that can be used in the context of the present invention is one wherein at least about 95% of the carbon-carbon bonds contained therein are single bonds; a preferred highly saturated fat is one having at least about 98% single-bonded carbon-carbon bonds; a more preferred highly saturated fat is one having at least about 99% single bond carbon-carbon bonds. Preferred highly saturated fats are commonly animal fats, such as, without limitation, mutton suet, pork lard or beef tallow, or combinations, or subfractions thereof. Such highly saturated fats need not be of animal origin. For example, waxes of plant, synthetic, and also animal origin can also be employed in the context of the present invention, so long as the selected wax exhibits the high saturation levels noted above.

Although the function of the fat used in the present invention is not fully elucidated, it is believed that the high degree of saturation of the fat used in the present invention, in addition to contributing to the lowering of the natural volatility of the clomazone, also contributes to the lowering of unintended and detrimental reactions that would likely occur between less-saturated solvents or fats and components of the wall of the microcapsule. These unintended and detrimental reactions are referred to as "fugitive reactions", and tend to disrupt the wall structure by forming strands that necessitate an additional filtration step in current clomazone formulation protocols. Generally, the fat used in the context of the present invention is a solid at room temperature, but dissolves in the presence of clomazone, which is a liquid. Accordingly, the clomazone acts as a solvent with the fat that is encased in the microcapsules of the present invention.

The highly saturated fat as used in the context of the present invention preferably constitutes from about 0.5 percent to about 12 percent by weight of the solution that is contained in the microcapsule, the remainder comprising clomazone and, optionally, other reagents included for purposes of densitization and stabilization of the formulation. Preferably, the solution of clomazone and highly saturated fat includes from about 1 percent to about 8 percent by weight of the highly saturated fat, and more preferably about 2 percent to about 6 percent.

The encapsulating walls of the microcapsules are made of a porous polymer, such as polyurea, polyamide, polysulfonamide, polyester, polycarbonate, or polyurethane and comprise from about 5 percent to about 35 percent by weight of each microcapsule. Preferably, the walls of the microcapsule comprise from about 10 percent to about 25 percent by weight of the microcapsule.

In a preferred embodiment of the present invention, the microcapsule preparation comprises an aqueous phase comprised of a solution containing a suitable emulsifier and an optional stabilizer, which is preferably an anti-foam agent, and an optional anti-microbial agent. The emulsifier is preferably selected from the group of the salts of ligninsulfonic acid, such as, for example, the sodium, potassium, magnesium, and calcium salts thereof. Particularly effective is the sodium salt of ligninsulfonic acid, which is referred to herein as a lignosulfonate emulsifier or surfactant. An organic phase comprising a solution of clomazone, an optional organic solvent, a highly saturated fat and a polyfunctional polyisocyanate, which is added to the composition of water, lignosulfonate surfactant, and optional anti-foam agent. Preferred organic solvents are selected, without limitation, from aromatic hydrocarbon solvents with flash points in the range of about 90° C. to about 250° C., hydrocarbon $C_{15}$–$C_{16}$ mixtures, $C_{14}$–$C_{16}$ alkyl biphenyl mixtures, aromatic esters, vegetable oils such as corn oil, soybean oil, soy salad oil, and hydro-treated oils; refined light paraffinic distillates, petroleum process oils, and mixtures and subfractions thereof. Particularly preferred solvents are selected from aromatic hydrocarbon solvents with flash points in the range of about 90° C. to about 250° C. A more particularly preferred solvent is a mixture of $C_9$–$C_{15}$ aromatic hydrocarbons with a flash point of about 95° C. Preferred, highly saturated fats are selected from animal fats that include suet, lard, and tallow. A particularly preferred fat is lard. The resulting mixture is stirred sufficiently under suitable conditions well-understood by those skilled in the art to form a homogenous dispersion of small droplets of the clomazone and fat solution within the aqueous phase.

Thereafter, in the preferred protocol, a polyfunctional amine is added with the stirring being continued until the polyfunctional amine has essentially fully reacted with the polyfunctional isocyanate. The polyfunctional isocyanate and the polyfunctional amine react in the presence of the surfactant under proper agitation and reaction conditions to form microcapsules having polyurea walls encapsulating the clomazone, optional solvent, and fat solution.

In a another embodiment of the present invention, the microcapsule preparation comprises an aqueous phase comprised of a solution containing a suitable emulsifier/cross-linking resin, an optional stabilizer in the form of an anti-foam agent, and an optional anti-microbial agent. The emulsifier/cross-linking resin is preferably derived from the copolymerization product of styrene and maleic anhydride, or derived from the copolymerization product of styrene, maleic anhydride and an alcohol. The copolymerization of styrene and maleic anhydride provides a non-esterified or anhydride copolymer. When the copolymerization of styrene and maleic anhydride is conducted with an alcohol, the maleic anhydride rings open to form a copolymer that is a half-acid and half-ester of the corresponding alcohol that is in the copolymerization reaction. Such alcohols include, without limitation, straight or branched chain lower $C_1$–$C_6$ alkyl alcohols. The anhydride copolymers and the half acid/half ester copolymers are further reacted with hydroxides such as ammonium hydroxide, sodium hydroxide, potassium hydroxide, magnesium hydroxide, calcium hydroxide, and the like, to provide the aforementioned resins in the form of water-soluble salts. Reaction of the aforementioned hydroxides with the anhydride copolymer causes the maleic anhydride rings to open to provide a di-salt, for example, a di-sodium salt or a di-potassium salt. When the anhydride copolymer is reacted with, for example, ammonium hydroxide, the maleic anhydride rings open to provide an amide/ammonium salt. In the context of the present invention, the emulsifier/cross-linking resin is preferably selected from the ammonium hydroxide, sodium hydroxide, potassium hydroxide, magnesium hydroxide, and calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half-acid/half-ester copolymerization product of styrene and maleic anhydride. Particularly preferred resins are the ammonium hydroxide and sodium hydroxide salts of an anhydrous copolymerization product of styrene and maleic anhydride, most preferred is the ammonium hydroxide salt.

An organic phase or solution of clomazone, an organic solvent, and a polyfunctional polyisocyanate is added to the composition of water, an emulsifier/cross-linking resin, an optional anti-foam agent, and an optional anti-microbial agent. The resulting mixture is stirred sufficiently under suitable conditions to form a homogenous dispersion of small droplets of the clomazone and organic solvent within the aqueous phase. Thereafter, a polyfunctional amine is added with the stirring being continued until the formation of the microcapsule having polyurea walls encapsulating the clomazone is complete. During the reaction of the polyfunctional amine with the polyfunctional isocyanate, cross-linking of the resin occurs. For example, the amide/ammonium salt moieties of the ammonium hydroxide salt of the anhydrous copolymerization product of styrene and maleic anhydride cross-link with the polyfunctional isocyanate during the microcapsule-forming reaction and become part of the porous polymer encapsulating wall. It is believed that the incorporation of the emulsifier/cross-linking resin into the encapsulating wall in the manner described, supra, promotes long-term physical stability of the formulation, inasmuch as the emulsifier has become part of the microcapsule, and cannot be physically removed by, for example, the exposure to the elements.

In a third embodiment of the present invention, the microcapsule preparation comprises an aqueous phase or solution containing an emulsifier/cross-linking resin as described, supra, an optional stabilizer in the form of an anti-foam agent, and an optional antimicrobial agent. An organic phase or solution of clomazone, a highly saturated fat, an organic solvent and a polyfunctional polyisocyanate is added to the composition of water, emulsifier/cross-linking resin, optional antifoam agent, and optional antimicrobial agent. The resulting mixture is stirred sufficiently under suitable conditions to form a homogenous dispersion of small droplets of the clomazone, fat, and organic solvent within the aqueous phase. Thereafter, a polyfunctional amine is added with stirring, during which time cross-linking of the resin occurs with the polyfunctional polyisocyanate as described supra.

The rate of the polymerization will depend on the reaction conditions employed. The rate of polymerization will generally be directly related to the temperature at which the reaction takes place.

The encapsulation process of the present invention is capable of satisfactory performance and production of encapsulated material without adjustment to a specific pH value. However, for purposes of enhanced stability the pH of the finished microencapsulated formulations is best maintained in a range of about 5.0 to about 8.0, preferably about 6.0 to about 7.5, more preferably about 6.5 to about 7.2. It may be desirable to further adjust the pH of the finished microcapsule formulation as, for example, when the aqueous base formulation of the microcapsules is combined with other herbicides, fertilizers, etc., conventional and suitable reagents for pH adjustment may be used. Such reagents include hydrochloric acid, acetic acid, phosphoric acid, sodium hydroxide, potassium hydroxide, ammonium hydroxide and the like.

The agitation employed to establish the dispersion of water immiscible phase droplets in the aqueous phase during the production of the formulation of the present invention may be supplied by any means capable of providing suitable high shear. That is to say that any variable shear mixing apparatus, e.g., a Waring Blender, a Brinkman Polytron homogenizer, Ross Model 100L homogenizer and the like can be usefully employed to provide the desired shear.

The particular size of the microcapsules for formulating the composition of the present invention will generally range from about one micron up to about one hundred microns in average diameter. From about one to about twenty microns is a preferred average range, in which a more preferred average range is about eight to about fourteen microns.

Salts and other compounds may be employed in the formulation. Salts and other compounds may: 1) act as antifreezes; 2) increase the ionic strength; and 3) function as densifiers in the aqueous phase. Examples of such salts include, without limitation, calcium chloride, sodium nitrate, and combinations thereof. Other compounds include, for example, urea that functions as an antifreeze when incorporated into the formulations of the present invention.

The microcapsules of clomazone as set forth herein are preferably suspended in an aqueous medium that preferably includes reagents that serve to keep the microcapsules from settling. These reagents, which form a suspension system composition, preferably comprise a combination of agents, such as surfactants, dispersants, emulsifiers, antifreeze agents, clays, water, salts, polymers, and other suspension stabilizing and density balancing agents, appropriately selected to keep the microcapsules in stable homogeneous suspension in the water-based carrier over an extended period of time, such as, for example, two years or more. The agents comprising the suspension system will generally comprise 0.01 percent by weight to 15 percent by weight of the formulation, preferably 1 percent to about 15 percent, more preferably 2 percent by weight to 10 percent by weight.

Many such agents can be used, and the optimum combination for each particular suspension system of active ingredient will vary. Suitable clays include bentonite clay and attapulgite clay and mixtures thereof, preferably in the range from about 0.01 percent to about 1.0 percent solid by weight, relative to the total formulation weight although greater or lesser amounts may be employed. The presence of at least one clay conventionally used in suspension systems improves the stability of the suspended microcapsules and particularly aids in the redistribution of the microcapsules upon shaking in the event some settling of microcapsules is experienced and redistribution thereof is required.

Another preferred suspension system also includes a small amount of a polysaccharide thickening agent to aid in stabilizing the suspension of the microcapsules. Xanthan gum is preferable, and is preferably present in an amount in the range from about 0.01 percent by weight to about 0.1 percent by weight although greater or lesser amounts may be employed.

The viscosity of the final product comprising the suspension system of the microcapsules of the present invention is preferably in the range of about 100 to about 4000 centipoise (cP), more preferably in the range of about 400 to 3000 cP, and most preferably, about 600 to about 2000 cP.

In the preferred final product about 100 to 750 grams of microcapsules (polymer plus encapsulated material) per liter of the composition and more preferably about 400 to about 600 grams microcapsules per liter are present. The encapsulating polymer component in the final encapsulated product normally will be in the range of about 0.2 percent by weight to about 12 percent by weight and preferably in the range of about 2 percent by weight to about 9 percent by weight.

Within the scope of this invention, polyisocyanates will be generally understood as meaning those compounds that contain two and more isocyanate groups in the molecule. Preferred isocyanates are di- and triisocyanates whose isocyanate groups may be linked to an aliphatic or aromatic moiety. Examples of suitable aliphatic diisocyanates and aliphatic triisocyanates are tetramethylene diisocyanate, pentamethylene diisocyanate, hexamethylene diisocyanate and 4-(isocyanatomethyl)-1,8-octyl diisocyanate. Suitable aromatic isocyanates are toluene diisocyanate (TDI: DESMODUR Registered TM VL, Bayer), polymethylene polyphenylisocyanate (MONDUR Registered TM MR, Miles Chemical Company); PAPI Registered TM 135 (Upjohn Company), 2,4,4'-diphenyl ether triisocyanate, 3,3'-dimethyl-4,4'-diphenyl diisocyanate, 3,3'-dimethoxy-4,4'diphenyl diisocyanate, 1,5-naphthalene diisocyanate and 4,4',4"-triphenylmethane triisocyanate. A further suitable diisocyanate is isophorone diisocyanate. Also suitable are adducts of diisocyanates with polyhydric alcohols, such as ethylene glycol, glycerol and trimethylolpropane, obtained by addition, per mole of polyhydric alcohol, of a number of moles of diisocyanate corresponding to the number of hydroxyl groups of the respective alcohol. In this way several molecules of diisocyanate are linked urethane groups to the polyhydric alcohol to form high molecular polyisocyanates. Another suitable product of this kind (DESMODUR Registered TM L) can be prepared by reacting three moles of toluene diisocyanate with one mole of 2-ethylglycerol (1,1-bismethylolpropane). Further suitable products are obtained by addition of hexamethylene diisocyanate or isophorone diisocyanate with ethylene glycol or glycerol. Preferred polyisocyanates are diphenylmethane-4,4'-diisocyanate and polymethylene polyphenylisocyanate. The di- and triisocyanates specified above can be employed individually or as mixtures of two or more such isocyanates.

Suitable polyamines within the scope of this invention will be understood as meaning in general those compounds that contain two or more primary amino groups in the molecule, which amino groups may be linked to aliphatic and aromatic moieties. Examples of suitable aliphatic polyamines are alpha,omega-diamines, including, without limitation, ethylenediamine, propylene-1,3-diamine, tetramethylenediamine, pentamethylenediamine and 1,6-hexamethylenediamine. A preferred diamine is 1,6-hexamethylenediamine.

Further suitable aliphatic polyamines are polyethyleneamines, including, without limitation, diethylenetriamine, triethylenetriamine, tetraethylenepentamine, pentaethylenehexamine.

Examples of suitable aromatic polyamines are 1,3-phenylenediamine, 2,4-toluylenediamine, 4,4'-diaminodiphenylmethane, 1,5-diaminoaphthalene, 1,3,5-triaminobenzene, 2,4,6-triaminotoluene, 1,3,6-triaminonaphthalene, 2,4,4'-triaminodiphenyl ether, 3,4,5-triamino-1,2,4-triazole, bis(hexamethylentriamine) and 1,4,5,8-tetra-aminoanthraquinone. Those polyamines which are insoluble or insufficiently soluble in water may be used as hydrochloride salts.

Yet further suitable polyamines are those that contain sulfo or carboxyl groups in addition to the amino groups. Examples of such polyamines are 1,4-phenylene diaminesulfonic acid, 4,4'-diaminodiphenyl-2-sulfonic acid, or diaminoammocarboxylic acids such as ornithene and lysine.

Suitable liquid fertilizers can be mixed with the formulations herein without the formation of unacceptable amounts of agglomerates in the spray tank, thus avoiding poor spraying performance. The liquid ferilizers used in mixtures of the present invention can be liquid nitrogen fertilizers, optionally containing phosphate and/or potash components. Liquid fertilizers are usually designated by the percentage weight of nitrogen, phosphorous and potassium (N—P—K) ratios, e.g., 4-10-10, 6-18-18, or 10-30-10.

The microcapsules of the present invention may be formulated with at least one other active ingredient. Such other active ingredient includes other pesticides such as herbicides and insecticides. Examples of such herbicides include dimethachlor, ametryn, pendimethalin, and trifluralin. Examples of such insecticides include bifenthrin, permethrin, cypermethrin, and organophosphates.

The present invention is better illustrated and is explained in more detail in the following examples wherein parts and percentages are given on a weight basis unless otherwise stated. It should be understood that the examples are merely illustrative of the invention and not limitative.

EXAMPLE I

This example illustrates the preparation of an aqueous suspension of microencapsulated clomazone in solution with a highly saturated fat.
Preparation of a Clomazone 3.0 CS Formulation Containing Animal Fat A pre-mixed aqueous phase consisting of 10.00 grams of the sodium salt of lignosulfonic acid (dispersant-Lignosol SFX65, from Lignotech; Rothchild, Wis.), and seven drops of a 100% polydimethyl siloxane (anti-foam agent-Dow Corning 1520US, from Ashland Chemical; Cleveland, Ohio) in 500.00 grams of water was placed in a 1000 mL beaker. The aqueous phase was homogenized at high speed (about 6000 rpm) for 60 seconds in a Brinkmann Polytron PT6000 blender, and a pre-mixed organic phase consisting of 20.00 grams of animal fat (solvent-lard, from Armour; Dallas, Tex.), 70.00 grams of polymethylenepolyphenyl isocyanate (wall-forming material-PAPI 27, from Dow Chemical; Midland, Mich.), 20.00 grams of a solvent consisting of a mixture of $C_9$–$C_{15}$ aromatic hydrocarbons with a flash point of about 95° C. (petroleum based solvent-Aromatic 200, from Exxon; Houston, Tex.), and 350.00 grams of clomazone (91% active ingredient) was added. Upon completion of addition, the high-speed blending was continued for about 120 minutes, then with medium stirring, 50.00 grams of 1,6-hexamethylenediamine (polymerizer-aqueous 70% HMDA from DuPont; Wilmington, Del.) in 50.00 grams of water was quickly injected into the aqueous/organic emulsion. With continued stirring, the temperature of the so-formed microcapsule suspension formulation was brought to about 60° C. during a 30 minute period, where it was maintained for about two hours. After this time, the formulation was cooled to ambient temperature and 50.00 grams of calcium chloride, 47.50 grams of sodium nitrate (densifiers-from Aldrich, Milwaukee, Wis.), and 20.00 grams of an aqueous 2% xanthum gum solution (thickener-Kelzan S from Kelco; Chicago, Ill.) was added to the formulation to promote the suspension of the microcapsules in water. Particle size: 10.4 microns (90%), Viscosity: 320 cP, pH: 7.0.

EXAMPLE II

This example illustrates the preparation of an aqueous suspension of microencapsulated clomazone where the microcapsule is formed in part from the reaction product of the amide/ammonium salt resin of an anhydrous copolymerization product of styrene and maleic anhydride and a polyfunctional polyisocyanate.
Preparation of a Clomazone 3.0 CS Formulation Containing a Resin Copolymer A pre-mixed aqueous phase consisting of 5.00 grams of an aqueous 25% solution of styrene maleic anhydride copolymer amide/ammonium salt (emulsifier/cross-linking-Scripset 720, from Solutia, Springfield, Mass.), 1.00 gram of a 100% polydimethyl siloxane (anti-foam agent-Dow Corning 1520US, from Ashland Chemical; Cleveland, Ohio), and 0.36 gram of an acidic 1.15% solution of a mixture of 2-methyl-4-isothiazolin-3-ones (a microbial growth inhibitor-Legend MK, from Rohm and Haas; Ambler, Pa.) in about 195.10 grams of water was placed in a 1000 ml vessel. The aqueous phase was homogenized at high speed (about 7000 rpm) for 10 seconds in a Brinkmann Polytron PT6000 blender, and a pre-mixed organic phase consisting of 210.00 grams of technical clomazone (90% active ingredient), 42.00 grams of polymethylenepolyphenyl isocyanate (wall-forming material-PAPI 27, from Dow Chemical; Midland, Mich.), and 24.00 grams of a solvent consisting of a mixture of $C_9$–$C_{15}$ aromatic hydrocarbons with a flash point of about 95° C. (petroleum based solvent-Aromatic 200, from Exxon; Houston, Tex.) was added at ambient temperature. Upon completion of addition, the high-speed blending was continued for about 10 seconds, then with medium stirring, 42.00 grams of an aqueous 35% solution of 1,6-hexamethylenediamine (polymerizer-aqueous 70% HMDA from DuPont; Wilmington, Del.) was quickly injected into the aqueous/organic emulsion. Upon completion of addition of the amine, the so-formed microcapsule suspension formulation was warmed to 60° C. where it stirred for 2 hours, and finally, the formulation was cooled to ambient temperature where it stirred for about 15 minutes. After this time, 24.00 grams of an aqueous 2% xanthum gum solution (thickener-Kelzan S from Kelco; Chicago, Ill.) was added to the formulation during a 15 minute period to promote the suspension of the microcapsules in water. To this was then added 42.00 grams of urea (widely available) as an antifreeze agent. The pH of the formulation was then adjusted to about 7.6 by the addition of about 5.00 grams of acetic acid (Aldrich, Milwaukee, Wis.). Particle size: 10.0 microns (90%), Viscosity; 900 cP, pH: 7.6.

EXAMPLE III

This example illustrates the preparation of an aqueous suspension of microencapsulated clomazone in solution with a highly saturated fat where the microcapsule is formed in part from the reaction product of the amide/ammonium salt resin of an anhydrous copolymerization product of styrene and maleic anhydride and a polyfunctional polyisocyanate.
Preparation of a Clomazone 3.0 CS Formulation Containing Animal Fat and a Resin Copolymer A pre-mixed aqueous phase consisting of 12.00 grams of an aqueous 25% solution of styrene maleic anhydride copolymer amide/ammonium salt (mulsifier/cross-linking-Scripset 720, from Solutia, Springfield, Mass.), 2.00 gram of a 100% polydimethyl siloxane (anti-foam agent-Dow Corning 1520US, from Ashland Chemical; Cleveland, Ohio), and 0.36 gram an acidic 1.15% solution of a mixture of 2-methyl-4-isothiazolin-3-ones (a microbial growth inhibitor-Legend MK, from Rohm and Haas, Ambler, Pa.) in about 204.64 grams of water was placed in a 1000 ml vessel. The aqueous phase was homogenized at high speed (about 7000 rpm) for 10 seconds in a Brinkmann Polytron PT6000 blender, and a pre-mixed organic phase consisting of 210.00 grams of technical clomazone (90% active ingredient), 30.00 grams of polymethylenepolyphenyl isocyanate (wall-forming material-PAPI 27, from Dow Chemical Company; Midland, Mich.)), 12.00 grams of animal fat (solvent-lard, from Armour; Dallas, Tex.) and 12.00 grams of a solvent consisting of a mixture of $C_9$–$C_{15}$ aromatic hydrocarbons with a flash point of about 95° C. (petroleum based solvent-Aromatic 200 from Exxon; Houston, Tex.) was added at 35° C. Upon completion of addition, the high-speed blending was continued for about 10 seconds, then, with medium stirring, 40.00 grams of an aqueous 35% solution of 1,6-hexamethylenediamine (polymerizer-aqueous 70% HMDA from DuPont, Wilmington, Del.) was quickly injected to the emulsion. Upon completion of addition of the amine, the so-formed microcapsule suspension formulation was warmed to 60° C. where it stirred for 2 hours, and finally, the formulation was cooled to ambient temperature where it stirred for about 15 minutes. After this time, 18.00 grams of an aqueous 2% Xanthum gum solution (thickener-Kelzan S from Kelco; Chicago, Ill.) was added to the formulation during a 15 minute period to promote the suspension of the microcapsules in water. To this was then added 60.00 grams of urea (widely available) as an antifreeze agent. The pH of the formulation was then adjusted to about 7.0 by the addition of about 3.50 grams of acetic acid (Aldrich, Milwaukee, Wis.). Particle size: 7.0 microns (90%), viscosity: 800 cP, pH: 7.0.

EXAMPLE IV

This example illustrates microencapsulated formulations of clomazone within the scope of the present invention wherein the components are expressed as ranges in weight/weight percents.

| CLOMAZONE 3.0 CS FORMULATIONS USING ANIMAL FATS AND/OR COPOLYMER RESIN | | | |
|---|---|---|---|
| | Percent weight/weight | | |
| Component Aqueous Phase | Formulations of Example I | Formulations of Example II | Formulations of Example III |
| Na salt of lignosulfonic acid (Dispersant) | 1.00–2.00 | — | — |

-continued

CLOMAZONE 3.0 CS FORMULATIONS USING ANIMAL FATS AND/OR COPOLYMER RESIN

Percent weight/weight

| Component Aqueous Phase | Formulations of Example I | Formulations of Example II | Formulations of Example III |
|---|---|---|---|
| Copolymer resin (Emulsifier/ cross-linking) | — | 0.20–1.00 | 0.20–1.00 |
| Anti-microbial agent | — | 0.02–0.10 | 0.02–0.10 |
| Anti-foam agent | 0.10–0.40 | 0.10–0.40 | 0.10–0.40 |
| Water (Diluent) Organic Phase | 27.82–47.26 | 29.82–52.12 | 28.82–48.06 |
| Polymethylene polyphenyl-isocyanate (Wall-forming material) | 4.50–8.00 | 4.50–8.00 | 4.50–8.00 |
| Animal fat (Solvent) | 2.00–3.00 | — | 2.00–3.00 |
| Petroleum-based hydrocarbon (Solvent) | 0.00–2.50 | 3.50–4.50 | 1.50–2.50 |
| Clomazone (90–99%) Amine Phase | 34.75–35.50 | 34.75–35.50 | 34.75–35.50 |
| 1,6-hexane-diamine (Polymerizer) | 1.90–5.00 | 1.90–5.00 | 1.90–5.00 |
| Water (Diluent) Post-encapsulation Components | 1.90–5.00 | 1.90–5.00 | 1.90–5.00 |
| Xanthan gum (Thickener) | 0.02–0.08 | 0.02–0.08 | 0.02–0.08 |
| Urea/CaCl$_2$/ NaNO$_3$ (Antifreeze/ densifier) | 5.00–10.00 | 5.00–10.00 | 5.00–10.00 |
| CH$_3$CO$_2$H (pH adjust) | 0.05–0.60 | 0.05–0.60 | 0.05–0.60 |

EXAMPLE V

The following example further illustrates the present invention, but, of course, should not be construed as in any way limiting its scope. The example sets forth certain biological data illustrating the efficacy of the microcapsule formulations when compared to the efficacy of similar formulations known in the art.

Seeds of barnyardgrass, giant foxtail, green foxtail, shatter-cane, and velvetleaf were planted in a 25 cm×15 cm×7.5 cm fiber flat containing topsoil. Each species was planted as a single row in the flat, which contained five rows. There were four replicate flats of the aforementioned weed species for each rate of application of clomazone test formulation. Stock solutions of each of the test formulations were prepared by dissolving a sufficient amount of formulation to provide 0.0356 grams of active ingredient in 40 mL of water. From the stock solution 20 mL was removed and serially diluted with 20 mL of water to provide application rates of 0.25, 0.125. 0.0625, 0.0313, 0.0156, and 0.0078 kg a.i./ha. The solutions of test formulation for each rate of application were then sprayed onto the surface of the soil using a track-sprayer m a spray hood. Flats were also sprayed as above with the same rates of a standard clomazone formulation sold as Command® Herbicide 4.0 Emulsifiable Concentrate (EC). Untreated controls were also included in each test. Upon completion of the spraying, the flats were placed in a greenhouse, where they were maintained for fourteen days. After this time, the test was visually evaluated for percent weed control. The percent weed control data for each test formulation and the standard Command Herbicide 4.0 EC formulation was subjected to regression analysis to determine the rate of application that would provide 85% weed control (ED$_{85}$) of each of the weed species. From these data the relative potency of the test formulation (the relative potency of the Command Herbicide 4.0 EC is one) was determined using the following ratio:

$$\text{Formulation Relative Potency} = \frac{\text{Formulation ED}_{85}}{\text{Command Herbicide ED}_{85}}$$

Formulation Relative Potency

| Formulation | Barnyardgrass | Giant Foxtail | Green Foxtail | Shatter-cane | Velvetleaf |
|---|---|---|---|---|---|
| Formulation of Example I | 1.03* | 1.43* | 1.09* | 1.22* | 1.94* |
| Formulation of Example II | 0.75 | 0.75 | 0.95 | 1.04 | 1.00 |
| Formulation of U.S. Pat. 5,783,520 | 0.42* | 0.75* | 0.59* | 0.60* | 0.54* |
| Command Herbicide 4EC | 1.00 | 1.00 | 1.00 | 1.00 | 1.00 |

*Average of two tests.

The formulations of Examples I and II of the present invention are generally equal in, if not more, herbicidally active than the standard Command Herbicide 4EC. The formulations of Example I and II are significantly more herbicidally active than the formulations of U.S. Pat. No. 5,783,520, ranging from about 1.1 to about 3.6 times more herbicidally active.

While the invention has been described in detail and with reference to specific embodiments thereof, it will be apparent to one skilled in the art that various changes and modifications can be made herein without departing from the spirit and scope thereof.

What is claimed is:

1. A herbicidal formulation consisting essentially of microcapsules suspended in an aqueous liquid, wherein (a) the microcapsules consist essentially of a porous polymer wall and clomazone, (b) the porous polymer wall consists essentially of the reaction product of a polyfunctional isocyanate, a cross-linking resin and a polyfunctional amine and (c) the cross-linking resin is selected from the group consisting of ammonium hydroxide, sodium hydroxide, potassium hydroxide, magnesium hydroxide, and calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half acid/half ester copolymerization product of styrene and maleic anhydride.

2. A herbicidal formulation as claimed in claim 1 wherein the cross-linking resin is selected from the group consisting of ammonium hydroxide and sodium hydroxide salts of an anhydrous copolymerization product of styrene and maleic anhydride.

3. The formulation of claim 1, wherein said porous polymer wall is from about 5% by weight to about 35% by weight of each microcapsule.

4. The formulation of claim 1, wherein said microcapsules are about 1 micron to about 100 microns in average diameter.

5. The formulation of claim 1, having a pH in the range of about 5.0 to about 8.0.

6. A method for preparing a herbicidal formulation as claimed in claim 1, consisting essentially of the following steps:
   (a) combining water and a cross-linking resin emulsifier selected from the group consisting of ammonium hydroxide, sodium hydroxide, potassium hydroxide, magnesium hydroxide, and the calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half-acid/half-ester copolymerization product of styrene and maleic anhydride;
   (b) adding a solution of clomazone, a polyisocyanate, and optionally an organic solvent.
   (c) emulsifying the solution; and
   (d) adding a polyfunctional amine; thereby generating the microcapsules containing a solution of clomazone, and optionally an organic solvent.

7. A method of controlling vegetation consisting essentially of spraying a herbicidally effective amount of the formulation as claimed in claim 1 to the surface of a selected plot containing vegetation to be controlled.

8. A method of controlling vegetation consisting essentially of spraying a herbicidally effective amount of the formulation as claimed in claim 2 to the surface of a selected plot containing vegetation to be controlled.

9. A herbicidal formulation consisting essentially of microcapsules suspended in an aqueous liquid, wherein (a) the microcapsules consists essentially of a porous polymer wall and clomazone, (b) the porous polymer wall consists essentially of the reaction product of a polyfunctional isocyanate, a cross-linking resin and a polyfunctional amine, (c) the cross-linking resin is selected from the group consisting of ammonium hydroxide, sodium hydroxide, potassium hydroxide, magnesium hydroxide, and calcium hydroxide salts of an anhydrous compolymerization product of styrene and maleic anhydride; and the ammonium hydroxide, sodium hydroxide, potassium hydroxide, magnesium hydroxide, and calcium hydroxide salts of a half acid/half ester copolymerization product of styrene and maleic anhydride, and (d) an emulsifier in said aqueous liquid.

10. The formulation of claim 9, wherein said emulsifier is a cross-linking resin selected from the group consisting of ammonium hydroxide, sodium hydroxide, potassium hydroxide, magnesium hydroxide, and calcium hydroxide salts of an anhydrous copolymerization product of styrene and maleic anhydride; and the ammonium hydroxide, sodium hydroxide, potassium hydroxide, magnesium hydroxide, and calcium hydroxide salts of a half acid/half ester copolymerization product of styrene and maleic anhydride.

11. The formulation of claim 9 wherein the emulsifier is a cross-linking resin selected from the group consisting of ammonium hydroxide and sodium hydroxide salts of an anhydrous copolymerization product of styrene and maleic anhydride.

12. A herbicidal formulation consisting essentially of microcapsules suspended in an aqueous liquid, wherein (a) the microcapsules consists essentially of a porous polymer wall and clomazone, (b) the porous polymer wall consists essentially of the reaction product of a polyfunctional isocyanate, a cross-linking resin and a polyfunctional amine, (c) the cross-linking resin is selected from the group consisting of ammonium hydroxide, sodium hydroxide, potassium hydroxide, magnesium hydroxide, and calcium hydroxide salts of an anhydrous compolymerization product of styrene and maleic anhydride; and the ammonium hydroxide, sodium hydroxide, potassium hydroxide, magnesium hydroxide, and calcium hydroxide salts of a half acid/half ester copolymerization product of styrene and maleic anhydride, and (d) an organic solvent.

13. The formulation of claim 12, wherein said solvent is a petroleum based mixture of $C_9$–$C_{15}$ aromatic hydrocarbons with a flash point of about 95° C.

* * * * *